US009995693B2

(12) United States Patent
Fujise et al.

(10) Patent No.: US 9,995,693 B2
(45) Date of Patent: *Jun. 12, 2018

(54) QUALITY EVALUATION METHOD FOR SILICON WAFER, AND SILICON WAFER AND METHOD OF PRODUCING SILICON WAFER USING THE METHOD

(71) Applicant: SUMCO CORPORATION, Tokyo (JP)

(72) Inventors: Jun Fujise, Tokyo (JP); Toshiaki Ono, Tokyo (JP)

(73) Assignee: SUMCO CORPORATION, Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/189,309

(22) Filed: Jun. 22, 2016

(65) Prior Publication Data

US 2016/0377554 A1     Dec. 29, 2016

(30) Foreign Application Priority Data

Jun. 26, 2015    (JP) ................. 2015-128970

(51) Int. Cl.
*C30B 33/00* (2006.01)
*G01N 21/95* (2006.01)
(Continued)

(52) U.S. Cl.
CPC ......... *G01N 21/9501* (2013.01); *C30B 29/06* (2013.01); *C30B 33/00* (2013.01);
(Continued)

(58) Field of Classification Search
CPC ......... C30B 33/00; C30B 33/02; C30B 15/00; C30B 29/06
See application file for complete search history.

(56) References Cited

U.S. PATENT DOCUMENTS

2010/0075267 A1* 3/2010 Sadohara ............ H01L 21/324
432/1

FOREIGN PATENT DOCUMENTS

JP    2008-103673 A    5/2008
JP    2011238664 A    11/2011
(Continued)

OTHER PUBLICATIONS

Leroy et al., "Warpage of Silicon Wafers", Journal of the Electrochemical Society, 1980, pp. 961, vol. 127.
(Continued)

*Primary Examiner* — Robert M Kunemund
(74) *Attorney, Agent, or Firm* — Greenblum & Bernstein, P.L.C.

(57) ABSTRACT

After determining the precipitated oxygen concentration and the residual oxygen concentration in a silicon wafer after heat treatment performed in a device fabrication process; the critical shear stress $\tau_{cri}$ at which slip dislocations are formed in the silicon wafer in the device fabrication process is determined based on the obtained precipitated oxygen concentration and residual oxygen concentration; and the obtained critical shear stress $\tau_{cri}$ and the thermal stress $\tau$ applied to the silicon wafer in the heat treatment of the device fabrication process are compared, thereby determining that slip dislocations are formed in the silicon wafer in the device fabrication process when the thermal stress $\tau$ is equal to or more than the critical shear stress $\tau_{cri}$, or determining that slip dislocations are not formed in the silicon wafer in the device fabrication process when the thermal stress $\tau$ is less than the critical shear stress $\tau_{cri}$.

8 Claims, 9 Drawing Sheets

(51) Int. Cl.
  *H01L 21/66*     (2006.01)
  *C30B 29/06*     (2006.01)
  *C30B 33/02*     (2006.01)
  *G01N 21/3563*   (2014.01)
  *H01L 21/322*    (2006.01)
  *G01N 21/35*     (2014.01)

(52) U.S. Cl.
  CPC .......... *C30B 33/02* (2013.01); *G01N 21/3563* (2013.01); *H01L 21/3225* (2013.01); *H01L 22/12* (2013.01); *G01N 2021/3568* (2013.01); *G01N 2021/3595* (2013.01); *G01N 2201/12* (2013.01)

(56) References Cited

FOREIGN PATENT DOCUMENTS

WO    2006-003812  A1    1/2006
WO    2008038786   A1    4/2008

OTHER PUBLICATIONS

Shimizu et al., "Warpage of Czochralski-Grown Silicon Wafers as Affected by Oxygen Precipitation", Japanese Journal of Applied Physics, 1985, pp. 815, vol. 24.

Sueoka et al., "Effect of Oxide Precipitate Sizes on the Mechanical Strength of Czochralski Silicon Wafers", Japanese Journal of Applied Physics, 1997, pp. 7095, vol. 36.

Korean Patent Office Action with respect to Korean Patent Application No. 10-2016-0079130 dated Apr. 28, 2017.

Taiwanese Office Action from Taiwanese Patent Application No. 105119401 dated Jul. 4, 2017.

Korean Office Action issued with respect to Application No. 10-2016-0079130, dated Nov. 30, 2017.

* cited by examiner

QUALITY EVALUATION METHOD FOR SILICON WAFER, AND SILICON WAFER AND METHOD OF PRODUCING SILICON WAFER USING THE METHOD

TECHNICAL FIELD

This disclosure relates to a quality evaluation method for a silicon wafer, and a silicon wafer and a method of producing a silicon wafer using the method. This disclosure relates in particular to a quality evaluation method for a silicon wafer making it possible to determine with high accuracy whether or not slip dislocations are formed after heat treatment is performed in a device fabrication process, and a silicon wafer and a method of producing a silicon wafer using the method.

BACKGROUND

For example, commonly, oxygen inevitably contained in a polished wafer made by the Czochralski (CZ) process is partly precipitated to form a gettering site in the device fabrication process.

Here, when heat treatment is performed on a silicon wafer, oxygen contained in the wafer reacts with silicon to form oxygen precipitates (bulk micro defects, BMDs). It is known that if this oxygen precipitation excessively proceeds, the mechanical strength of the silicon wafer decreases, slip dislocations are formed even under low load stress in the device fabrication process, and the wafer is warped (for example, see NPL 1 (B. Leroy and C. Plougonven, Journal of the Electrochemical Society, 1980, Vol. 127, p. 961) and NPL 2 (Hirofumi Shimizu, Tetsuo Watanabe and Yoshiharu Kakui, Japanese Journal of Applied Physics, 1985, Vol. 24, p. 815)). Further, NPL 3 (Koji Sueoka, Masanori Akatsuka, Katahama and Naoshi Adachi, Japanese Journal of Applied Physics, 1997, Vol. 36, p. 7095) describes that a larger size of BMDs increases the formation of slip dislocations caused when a thermal stress is applied to a wafer.

Since such a formation of slip dislocations caused in a device fabrication process reduces the yield of silicon devices, it is important to provide a silicon wafer in which slip dislocations are not formed even after heat treatment in the device fabrication process is performed. With respect to the control of such slip dislocations, WO 2006/003812 A (PTL 1) describes that a reduced size of BMDs increases the stress causing the formation of slip dislocations from the BMDs, which suppresses the reduction in the strength of the silicon wafer caused by oxygen precipitations.

Further, JP 2008-103673 A (PTL 2) describes that BMDs having a small size are densely formed in the wafer and the density of BMDs having a large size is minimized, thereby effectively suppressing the formation of slip dislocations.

CITATION LIST

Patent Literature

PTL 1: WO 2006/003812 A
PTL 2: JP 2008-103673 A

Non-Patent Literature

NPL 1: B. Leroy and C. Plougonven, Journal of the Electrochemical Society, 1980, Vol. 127, p. 961

NPL 2: Hirofumi Shimizu, Tetsuo Watanabe and Yoshiharu Kakui, Japanese Journal of Applied Physics, 1985, Vol. 24, p. 815

NPL 3: Koji Sueoka, Masanori Akatsuka, Hisashi Katahama and Naoshi Adachi, Japanese Journal of Applied Physics, 1997, Vol. 36, p. 7095

SUMMARY

In recent years, since rapid heating and cooling processes are mostly used in silicon device fabrication processes, silicon wafers are subjected to more severe thermal stress than conventional ones, which results in an environment in which slip dislocations are easily formed in the silicon wafers.

PTLs 1 and 2 describe the association of the size and the density of BMDs with the formation of slip dislocations; however, the methods of PTLs 1 and 2 are not sufficiently capable of preventing the formation of slip dislocations under such a severe environment.

Given the facts, it could be helpful to propose a quality evaluation method for a silicon wafer making it possible to determine with high accuracy whether or not slip dislocations are formed after heat treatment is performed in a device fabrication process, and a silicon wafer and a method of producing a silicon wafer using the method.

The inventors of this disclosure diligently studied ways to solve the above problems. In a previous application (JP 2011-238664 A, JP 5533210 B), the inventors proposed a heat treatment method in which suitable heat treatment is performed on a silicon wafer in the wafer production stage in order to prevent slip dislocations from being formed in a device fabrication process. Further, they found that the critical shear stress $\tau_{cri}$ at which slip dislocations are formed in the device fabrication process is closely related to the ratio of the residual oxygen concentration $C_O$ (concentration of oxygen left in a wafer having been subjected to heat treatment performed in the wafer production stage) with respect to the BMD size L, expressed as $C_O/L$ (that is, the product of the reciprocal of L, i.e., $1/L$ and $C_O$).

However, whereas the size L of BMDs in a silicon wafer increases as time passes, the residual oxygen concentration $C_O$ decreases. In other words, as time passes, the critical shear stress $\tau_{cri}$ at which slip dislocations are formed decreases, which causes slip dislocations to be easily formed. Accordingly, in order to produce a silicon wafer in which slip dislocations are not formed in the device fabrication process, considering the change of the BMD size L and the residual oxygen concentration $C_O$ in the device fabrication process, it is important to find the critical shear stress $\tau_{cri}$ based on the BMD size L and the residual oxygen concentration $C_O$ "after the heat treatment performed in the device fabrication process".

The BMD size L is typically measured using a transmission electron microscope (TEM), which results in the variations in the measured values and furthermore takes a long time for the measurement. To address these problems, the inventors conceived of measuring the precipitated oxygen concentration $\Delta O_i$ in place of the BMD size L. That is, the BMD size L and the precipitated oxygen concentration $\Delta O_i$ have a ratio of 1:1, and the BMD size L is proportional to the precipitated oxygen concentration $\Delta O_i$. Further, since the measurement of the precipitated oxygen concentration $\Delta O_i$ is performed by measuring the value of the whole bulk using a Fourier transform infrared spectrometer (FT-IR), the measured values are less varied and the measurement itself is significantly simple. For this reason, they conceived of measuring the precipitated oxygen concentration $\Delta O_i$ in place of the BMD size L.

Further, as a result of further studies to determine the critical shear stress $\tau_{cri}$ with higher accuracy, the inventors found that it is significantly effective to formulate the critical shear stress $\tau_{cri}$ as the sum of the reciprocal of the precipitated oxygen concentration $\Delta O_i$, i.e., $1/\Delta O_i$ and the residual oxygen concentration $C_O$ in a silicon wafer after heat treatment performed in the device fabrication process. They also found that a comparison of the critical shear stress $\tau_{cri}$ estimated by the thus obtained formula and the thermal stress $\tau$ applied to a silicon wafer in heat treatment of the device fabrication process makes it possible to determine whether or not slip dislocations are formed in the device fabrication process and to evaluate the quality (determine the pass/fail) of the silicon wafer. Thus, they accomplished the present invention.

Specifically, we propose the following features.

(1) A quality evaluation method for a silicon wafer, comprising the steps of:

determining the precipitated oxygen concentration and the residual oxygen concentration in a silicon wafer after heat treatment performed in a device fabrication process;

determining the critical shear stress $\tau_{cri}$ at which slip dislocations are formed in the silicon wafer in the device fabrication process based on the obtained precipitated oxygen concentration and residual oxygen concentration; and comparing the obtained critical shear stress $\tau_{cri}$ and the thermal stress $\tau$ applied to the silicon wafer in the heat treatment of the device fabrication process, whereby determining that slip dislocations are formed in the silicon wafer in the device fabrication process when the thermal stress $\tau$ is equal to or more than the critical shear stress $\tau_{cri}$, or determining that slip dislocations are not formed in the silicon wafer in the device fabrication process when the thermal stress $\tau$ is less than the critical shear stress $\tau_{cri}$.

(2) The quality evaluation method for a silicon wafer, according to (1) above, wherein the critical shear stress $\tau_{cri}$ is given by Formula (A) below, where $\Delta O_i$: the precipitated oxygen concentration, $C_O$: the residual oxygen concentration, T: the temperature of the heat treatment, and k: the Boltzmann constant.

$$\tau_{cri} = 24.6 \times (1/\Delta O_i) + 7.0 \times 10^{-5} \times C_O \times \exp(0.91\ eV/kT) \quad (A)$$

(3) The quality evaluation method for a silicon wafer, according to (1) above, wherein the step of determining the precipitated oxygen concentration $\Delta O_i$ and the residual oxygen concentration $C_O$ after heat treatment in the device fabrication process is performed by measuring the precipitated oxygen concentration and the residual oxygen concentration in the silicon wafer after the heat treatment performed on the silicon wafer in the device fabrication process.

(4) The quality evaluation method for a silicon wafer, according to (1) above, wherein the step of determining the precipitated oxygen concentration and the residual oxygen concentration $C_O$ after the heat treatment in the device fabrication process is performed by simulation calculation.

(5) The quality evaluation method for a silicon wafer, according to (1) above, wherein the thermal stress $\tau$ is estimated based on the temperature distribution in the radial direction of the silicon wafer having been heated by being loaded into a heat treatment unit.

(6) The quality evaluation method for a silicon wafer, according to (1) above, wherein the thermal stress $\tau$ is estimated by simulation calculations.

(7) A method of producing a silicon wafer, comprising the steps of:

growing a single crystal silicon ingot under the growing conditions allowing a silicon wafer to be obtained, which wafer is determined to have no slip dislocations formed in a device fabrication process by the quality evaluation method for a silicon wafer, according to (1) above and subjecting the grown single crystal silicon ingot to a wafer processing process.

(8) The method of producing a silicon wafer, according to (7) above, wherein the precipitated oxygen concentration after heat treatment in the device fabrication process is $0.06 \times 10^{17}$ atoms/cm$^3$ or more and $0.8 \times 10^{17}$ atoms/cm$^3$ or less.

(9) The method of producing a silicon wafer, according to (7) above, wherein the residual oxygen concentration after heat treatment in the device fabrication process is $10 \times 10^7$ atoms/cm$^3$ or more and $18 \times 10^{17}$ atoms/cm$^3$ or less.

(10) A silicon wafer having a precipitated oxygen concentration and a residual oxygen concentration, at which the thermal stress $\tau$ obtained in a device fabrication process is lower than the critical shear stress $\tau_{cri}$ at which slip dislocations are formed in the device fabrication process.

(11) The silicon wafer according to (10) above, wherein the precipitated oxygen concentration after heat treatment in the device fabrication process is $0.06 \times 10^{17}$ atoms/cm$^3$ or more and $0.8 \times 10^{17}$ atoms/cm$^3$ or less.

(12) The silicon wafer according to (10) above, wherein the residual oxygen concentration after heat treatment in the device fabrication process is $10 \times 10^{17}$ atoms/cm$^3$ or more and $18 \times 10^{17}$ atoms/cm$^3$ or less.

Thus, the critical shear stress at which slip dislocations are formed in a device fabrication process is determined with high accuracy, thereby determining with high accuracy whether or not slip dislocations are formed in a silicon wafer due to heat treatment of the device fabrication process.

DETAILED DESCRIPTION (Quality Evaluation Method for Silicon Wafer)

Figure 1:
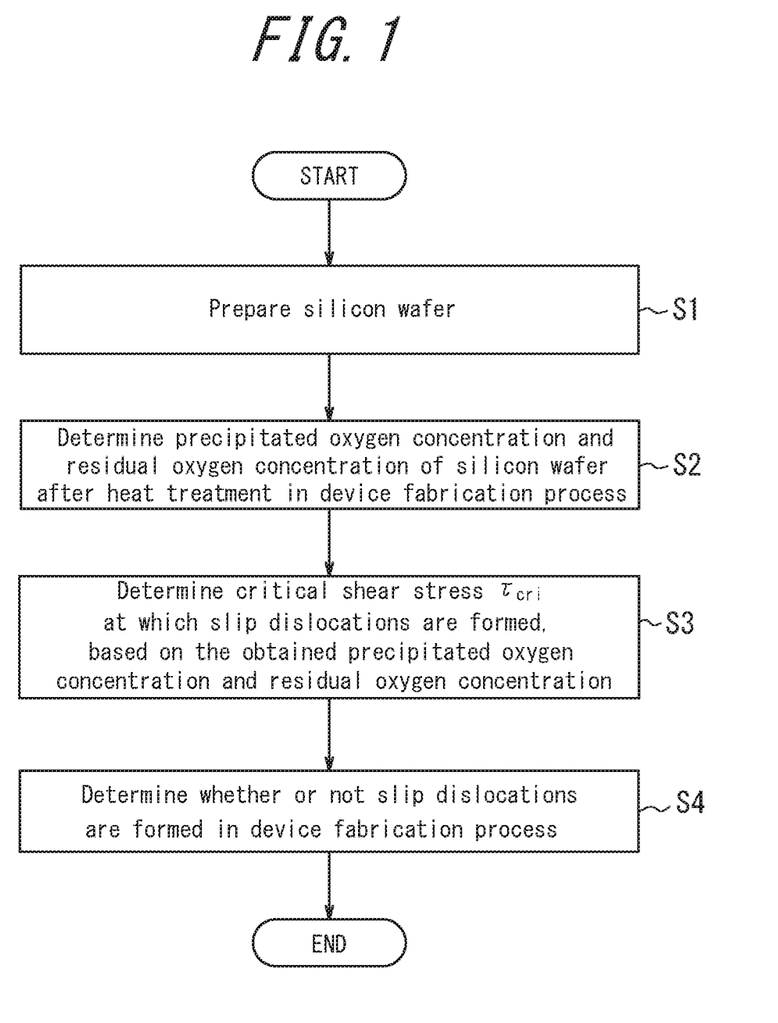
FIG. 1 is a flowchart of one embodiment of a quality evaluation method for a silicon wafer.

Embodiments will now be described with reference to the drawings. FIG. 1 shows a flowchart of one embodiment of a quality evaluation method for a silicon wafer. First, a silicon wafer W is prepared in Step S1. For the silicon wafer W, a silicon wafer having a predetermined thickness can be used, which wafer is obtained by a known processing process including peripheral grinding, slicing, lapping, etching, and mirror polishing performed on a single crystal silicon ingot I grown by the CZ process or the floating zone melting (FZ) process. In the growth of the single crystal silicon ingot I, the oxygen concentration, the carbon concentration, the nitrogen concentration, and the like can be suitably adjusted so that the silicon wafer W cut out of the grown silicon ingot I will have the desired characteristics. Further, suitable dopants may be added to obtain a wafer having a conductivity type of n-type or p-type.

Next, the precipitated oxygen concentration $\Delta O_i$ and the residual oxygen concentration $C_O$ in the silicon wafer W after heat treatment performed in the device fabrication process are determined in Step S2. Here, the precipitated oxygen concentration $\Delta O_i$ and the residual oxygen concentration $C_O$ in the silicon wafer W "after heat treatment performed in the device fabrication process" are determined.

The precipitated oxygen concentration $\Delta O_i$ and the residual oxygen concentration $C_O$ "after heat treatment in the device fabrication process" herein can be determined by actually performing a heat treatment performed in a device fabrication process on the silicon wafer W or a heat treatment designed to emulate the heat treatment performed in the device fabrication process and by measuring the precipitated oxygen concentration $\Delta O_i$ and the residual oxygen concentration $C_O$ after the heat treatment. Such a heat treatment can be performed using a rapid thermal annealing (RTA) system or the like.

In this disclosure, when a heat treatment performed in a device fabrication process includes a plurality of steps, the heat treatment temperature is the temperature at which the thermal stress $\tau$ is highest.

The residual oxygen concentration $C_O$ of oxygen left in the silicon wafer W and the precipitated oxygen concentration $\Delta O_i$ after such a heat treatment is measured based on the infrared absorption spectroscopy in accordance with ASTM F121-1979 using a Fourier transform infrared spectrometer (FT-IR).

Alternatively, the precipitated oxygen concentration $\Delta O_i$ and the residual oxygen concentration $C_O$ after heat treatment can be obtained by simulation calculation without actually performing heat treatment on the silicon wafer W in the device fabrication process. Specifically, the above values can be obtained using a known numerical analysis technique (for example, see Sumio Kobayashi. Journal of Crystal Growth, 1997, Vol. 174, p. 163). Using such simulation calculation, as compared with the case of performing heat treatment on the silicon wafer W, the precipitated oxygen concentration $\Delta O_i$ and the residual oxygen concentration $C_O$ can be determined more simply and in a shorter time.

Note that when the precipitated oxygen concentration $\Delta O_i$ and the residual oxygen concentration $C_O$ after heat treatment performed in the device fabrication process are determined by simulation calculation, the silicon wafer W need not be actually prepared in Step S1. Namely, Step S1 can be omitted, and only the data of the initial oxygen concentration, the thermal history during the growth, and the dopant concentration of a single crystal silicon ingot grown under certain conditions are required.

Subsequently, in Step S3, the critical shear stress $\tau_{cri}$ at which slip dislocations are formed in the silicon wafer in the device fabrication process is determined based on the precipitated oxygen concentration $\Delta O_i$ and the residual oxygen concentration $C_O$ determined in Step S2. As described above, in the previous application (JP 2011-238664 A, JP 5533210 B), the inventors found that the critical shear stress $\tau_{cri}$ at which slip dislocations are formed in a device fabrication process is closely related to the ratio of the residual oxygen concentration $C_O$ (concentration of oxygen left in a wafer having been subjected to heat treatment performed in the wafer production stage) with respect to the BMD size L, expressed as $C_O/L$ (that is, the product of the reciprocal of L, i.e., $1/L$ and $C_O$).

As a result of further studies to determine $\tau_{cri}$ with higher accuracy, the inventors found that it is significantly effective to measure the precipitated oxygen concentration $\Delta O_i$ in place of the BMD size L and formulate the critical shear stress $\tau_{cri}$, at which slip dislocations are formed in the device fabrication process, as the sum of the reciprocal of the precipitated oxygen concentration $\Delta O_i$, i.e., $1/\Delta O_i$ and the residual oxygen concentration $C_O$ in a silicon wafer after heat treatment performed in the device fabrication process. Experiments that made it possible to obtain the above finding will now be described.

Figure 2:
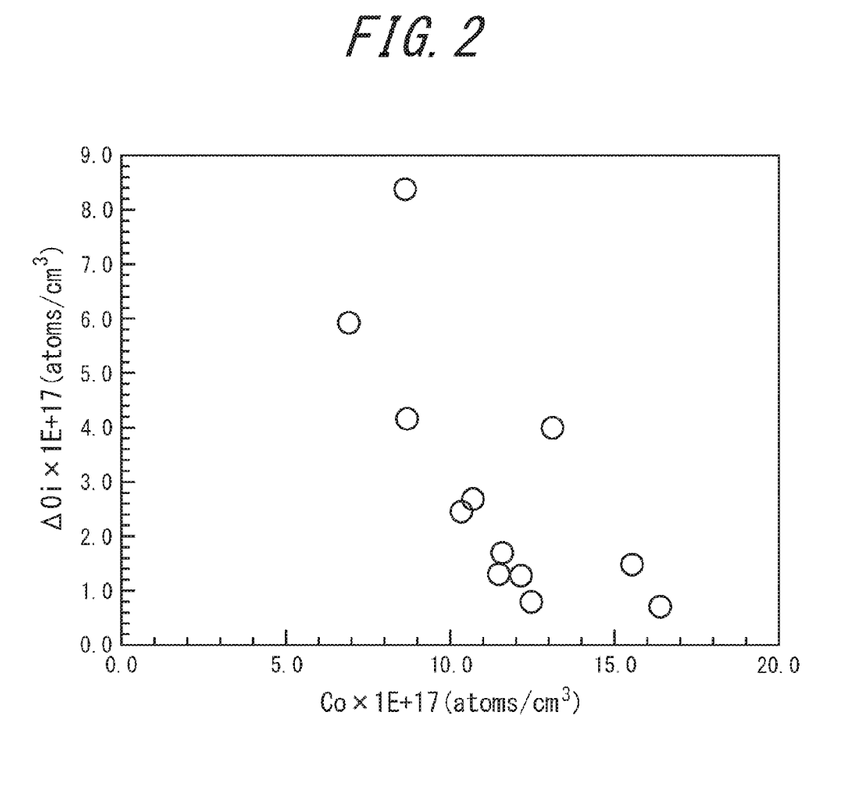
FIG. 2 is a diagram showing the relationship between the residual oxygen concentration and the precipitated oxygen concentration of sample wafers.

First, a number of samples of silicon wafers shown in FIG. 2 (hereinafter referred to as "sample wafer(s)") that have different precipitated oxygen concentrations $\Delta O_i$ and residual oxygen concentrations $C_O$ were prepared. These sample wafers were subjected to a high-temperature three-point bending test at a temperature in the range of 700° C. to 1200° C. The "high-temperature three-point bending test" is a method in which a stress can be applied to sample wafers at a given temperature, which makes it possible to determine the critical shear stress $\tau_{cri}$ at which slip dislocations are formed at the temperature to be determined.

Figure 3:
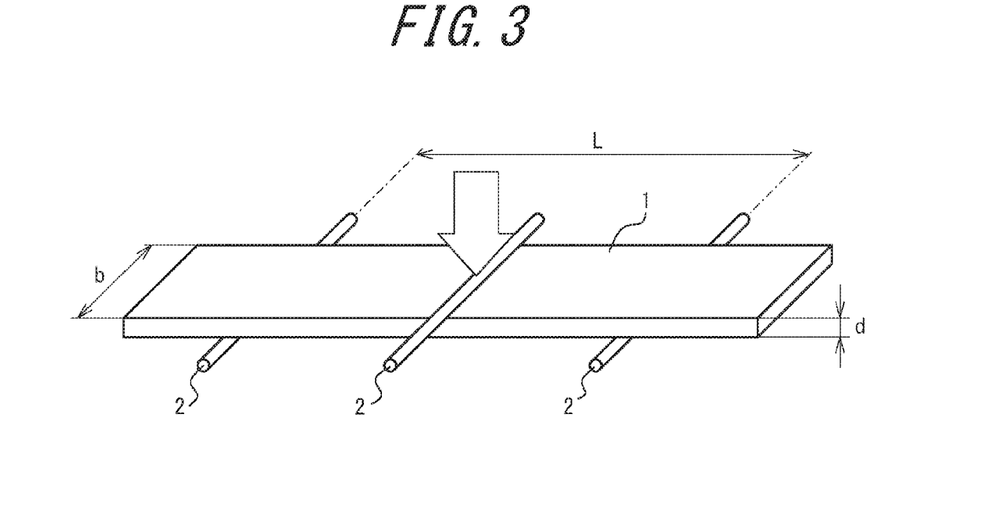
FIG. 3 is a diagram illustrating a high-temperature three-point bending test.
Figure 4:
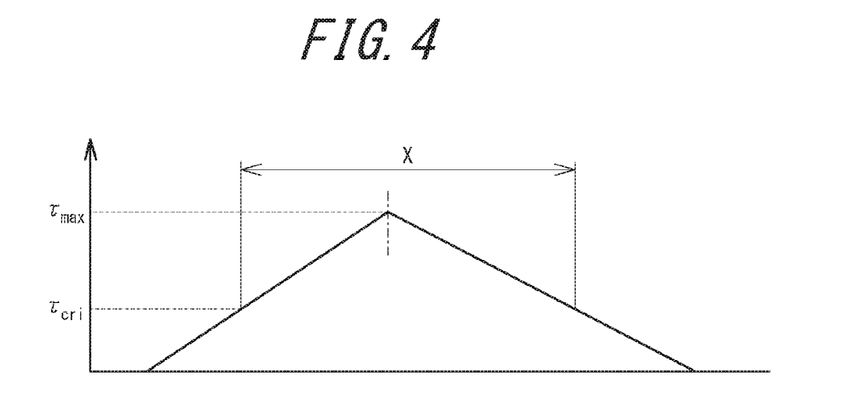
FIG. 4 is a diagram showing the profile of the stress applied to sample wafers in the high-temperature three-point bending test.

Specifically, each sample wafer was cut out in a 10 mm×40 mm piece and the obtained sample piece 1 was placed on support rods 2 with their support points at intervals of 30 mm as shown in FIG. 3. The thus placed sample piece 1 was placed in a heat treatment furnace (not shown), which was set to a given temperature, and was loaded with a stress as shown in FIG. 3. After being loaded with the stress, the sample piece 1 was cooled to room temperature and taken out to be subjected to selective etching, which caused slip dislocations to be formed from BMDs. Since the slip locations became visible as a band of dislocation pits with the point of action being the center, the width of the band of the visible dislocation pits was measured. In the three-point bending test, the stress has a profile shown in FIG. 4. The limit stress at which dislocation pits are formed, that is, the critical stress of slip dislocations formed from BMDs, is a stress applied to edges of the band. Accordingly, $\tau_{cri}$ can be determined from the formula (1) below.

$$\tau_{cri} = \tau_{max} \times (L/L - X) \qquad (1),$$

where $\tau_{max}$ is the shear stress applied to the sample piece 1 in the test, L is the distance between the support points, and X is the width of the band of the dislocation pits. In this test, the applied load is read using a load cell and the read value was converted to the shear stress. Slip dislocations in silicon are formed on the (111) plane in the <110> direction.

Considering this, the maximum shear stress $\tau_{max}$ was determined by the following formula.

$$\tau_{max}=(3\times P\times L)/(2\times b\times d^2)\times 0.40825 \quad (2),$$

where P is the maximum load read by the load cell, b is the width of the sample piece 1, and d is the thickness of the sample piece 1. Using the method, the maximum shear stress $\tau_{max}$ was calculated, and the distance between the support points and the width of the dislocation pits were measured, thereby calculating the critical shear stress $\tau_{cri}$.

Figure 5:
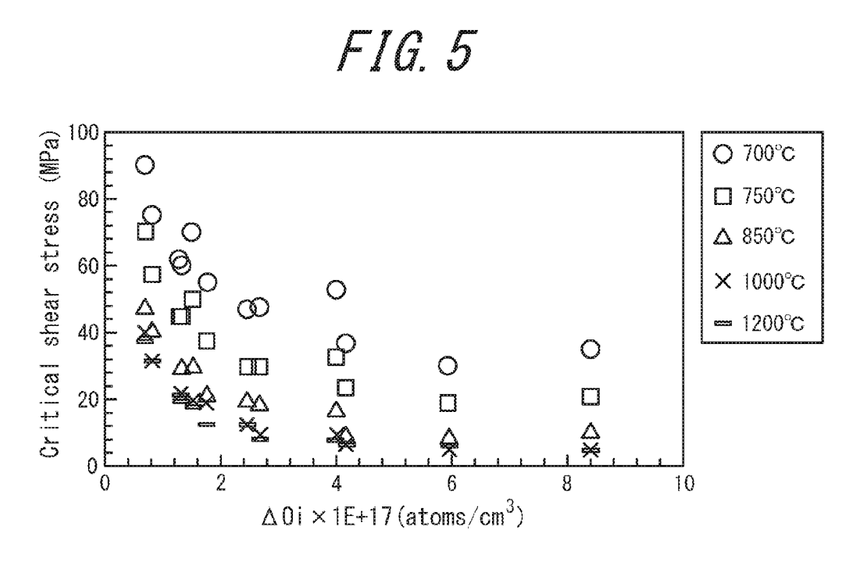
FIG. 5 is a diagram showing the relationship between the precipitated oxygen concentration and the critical shear stress obtained in the high-temperature three-point bending test.
Figure 6:
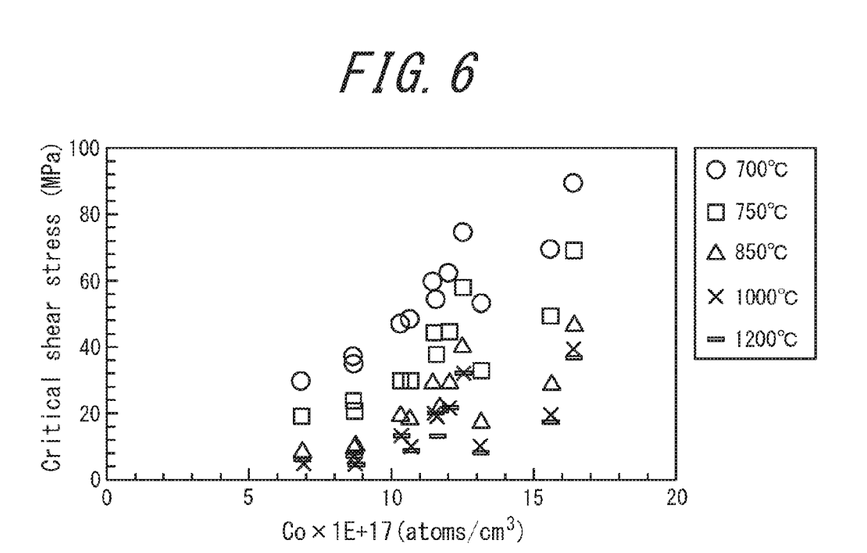
FIG. 6 is a diagram showing the relationship between the residual oxygen concentration and the critical shear stress obtained in the high-temperature three-point bending test.

FIG. 5 shows the relationship between the precipitated oxygen concentration $\Delta O_i$ and the critical shear stress $\tau_{cri}$ of the sample wafers, estimated in the high-temperature three-point bending test. This diagram shows that the critical shear stress $\tau_{cri}$ decreases as the precipitated oxygen concentration $\Delta O_i$ increases. FIG. 6 shows the relationship between the residual oxygen concentration $C_O$ and the critical shear stress $\tau_{cri}$ of the sample wafers, estimated in the high-temperature three-point bending test. This diagram shows that the critical shear stress $\tau_{cri}$ decreases as the residual oxygen concentration $C_O$ decreases.

From the relationship between the precipitated oxygen concentration $\Delta O_i$ and the critical shear stress $\tau_{cri}$ shown in FIG. 5, the effect of the precipitated oxygen concentration $\Delta O_i$ on the critical shear stress $\tau_{cri}$ can be expressed by the formula (3) below.

$$\tau_{\Delta O}=A(1/\Delta O_i) \quad (3),$$

where A is a constant and $\Delta O_i$ is the precipitated oxygen concentration.

Meanwhile, the effect of change in the residual oxygen concentration $C_O$ on the critical shear stress $\tau_{cri}$ can be regarded as the behavior of the stress (locking force) by which oxygen in the BMDs locks (closely holds) punched-out dislocations serving as Frank-Read sources. The locking force can be expressed by the formula (4) below.

$$\tau_{SL}=B\times C_O\times\exp(0.91\ eV/kT) \quad (4),$$

where B is a constant, k is the Boltzmann constant, and T is the temperature.

The combination of those two formulae is considered to make it possible to express the critical shear stress $\tau_{cri}$. For example, $\tau_{cri}$ can be expressed as the product of $\tau_{\Delta O_i}$ and $\tau_{SL}$. However, in that case, the critical shear stress $\tau_{cri}$ is 0 if the residual oxygen concentration $C_O$ is 0, and this is physically unnatural because slip dislocations are formed without a load of stress. Accordingly, the inventors conceived of formulating $\tau_{cri}$ as the sum of $\tau_{\Delta O_i}$ and $\tau_{SL}$. Specifically, the critical shear stress $\tau_{cri}$ is formulated as the formula (5) below.

$$\tau_{cri}=\tau_{\Delta O_i}+\tau_{SL}=A(1/\Delta O_i)+B\times C_O\times\exp(0.91\ eV/kT) \quad (5)$$

In the above formula (5), the critical shear stress $\tau_{cri}$ at which slip dislocations are formed in the device fabrication process is expressed as the sum of the stress component $\tau_{\Delta O_i}$ required for the formation of slip dislocations from punched-out dislocations caused by BMDs and the stress component $\tau_{SL}$ for releasing the formed punched-out dislocations from the locking by oxygen in the BMDs. Further, as shown in Examples below, the critical shear stress $\tau_{cri}$ at which slip dislocations are formed in the device fabrication process can be estimated with exceedingly high accuracy by the above formula (5).

Figure 7:
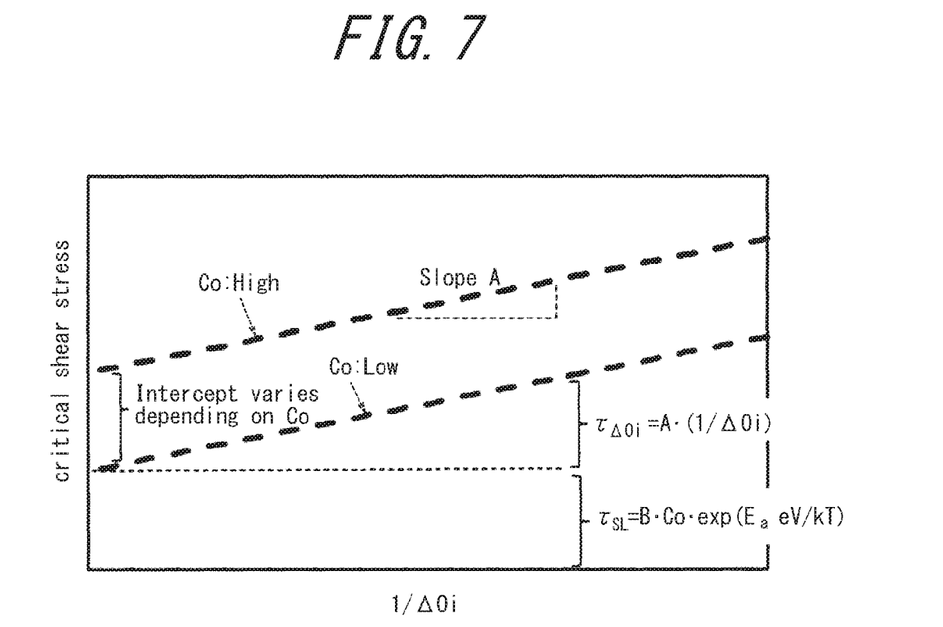
FIG. 7 is a diagram illustrating the terms in the formula of the critical shear stress, used in this disclosure.

This formula (5) will be described in more detail with reference to FIG. 7. FIG. 7 shows a configuration image of the formula (5) in which the two broken lines show the behavior of the critical shear stress $\tau_{cri}$ of when the precipitated oxygen concentration $\Delta O_i$ varies depending on different residual oxygen concentrations $C_O$ in the formula (5). As described above, in the formula (5), the second term $\tau_{SL}$ represents the locking force of the punched-out dislocations formed from the BMDs, which varies depending on $C_O$. According to the formula (5), even if the precipitated oxygen concentration $\Delta O_i$ on the horizontal axis is infinitely large, slip dislocations are not formed unless a stress exceeding the locking force is applied. The effect of the precipitated oxygen concentration $\Delta O_i$ is represented by a slope A only after a stress exceeding the locking force is applied. As the precipitated oxygen concentration $\Delta O_i$ is lower, slip dislocations are not formed unless a higher stress is applied.

As a result of determining the constants A and B in the above formula (5) by the regression analysis, the critical shear stress $\tau_{cri}$ at which slip dislocations are formed in the device heat treatment process is expressed as in the formula (6) below.

$$\tau_{cri}=24.6\times(1/\Delta O_i)+7.0\times10^{-5}\times C_O\times\exp(0.91\ eV/kT) \quad (6)$$

Figure 8:
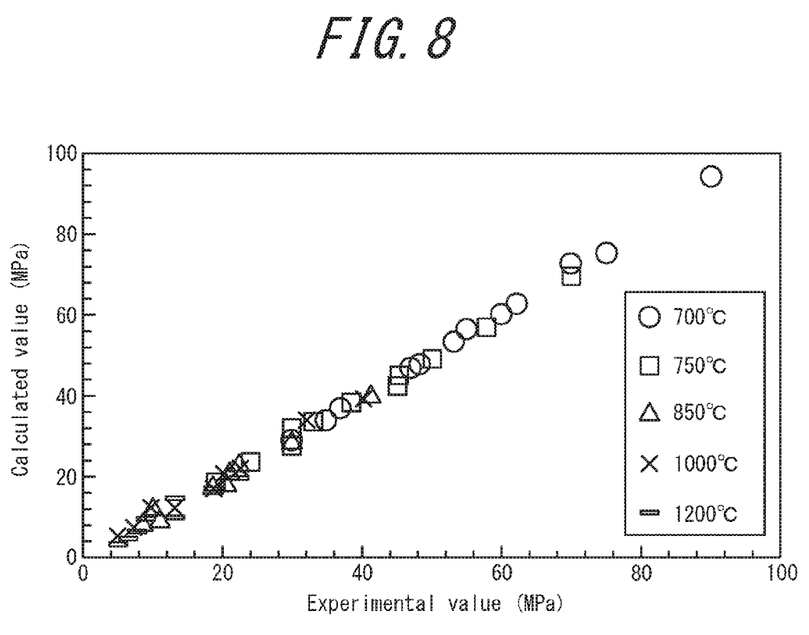
FIG. 8 is a diagram showing the relationship between the experimental value and the calculated value of the critical shear stress.

FIG. 8 shows the relationship between the calculated value of the critical shear stress $\tau_{cri}$ obtained by the above formula (6) and the experimental value thereof obtained from the above-described high-temperature three-point bending test. This diagram shows that the critical shear stress $\tau_{cri}$ within the temperature range of 700° C. to 1200° C. can be calculated with good reproducibility using the above formula (6). Here, the critical shear stress $\tau_{cri}$ at which slip dislocations are formed in the device fabrication process is determined using the above formula (6).

Subsequently, the obtained critical shear stress $\tau_{cri}$ and the thermal stress $\tau$ applied to the silicon wafer W in the device fabrication process are compared. The thermal stress $\tau$ applied to the silicon wafer in the device fabrication process can be determined as follows. Specifically, first, the silicon wafer is loaded into a heat treatment unit such as an RTA apparatus to heat the silicon wafer to apply thermal stress thereto. Under the heating conditions in normal RTA, the heating distribution is adjusted so that the temperature does not vary in the wafer plane; however, here, thermal stress is designed to be generated with an uneven heating profile. Next, the temperature distribution T(r') in the radial direction of the silicon wafer is measured using a thermocouple. The stresses in the radial direction and the circumferential direction are given by the following respective formulae (7) and (8).

$$\sigma_r(r)=\alpha E\left\{\frac{1}{R^2}\int_0^R T(r')r'dr'-\frac{1}{r^2}\int_0^r T(r')r'dr'\right\} \quad (7)$$

$$\sigma_\theta(r)=\alpha E\left\{-T(r)+\frac{1}{R^2}\int_0^R T(r')r'dr'+\frac{1}{r^2}\int_0^r T(r')r'dr'\right\}, \quad (8)$$

where r is the position in the radial direction of the silicon wafer, and R is the radius of the silicon wafer, $\alpha$ is the coefficient of thermal expansion, and E is the Young's modulus.

In a single crystal body like a silicon wafer, the planes and the direction in which slip dislocations are formed are limited, so that an analysis considering the slip planes is required. Slip dislocations in silicon are formed on the {111} planes in the <110> direction. Excluding the equivalents, there are three slip slopes in the <110> direction each for four {111} planes. Accordingly, 12 types of shear stresses are required to be determined.

The stress estimated using the above cylindrical coordinate system is converted to the Cartesian coordinate system, thereby determining the shear stresses on the respective slip planes in the respective slip directions as in the formula (9) below. Note that a slip plane is denoted by (ijk) and the slip direction is denoted by [1 mm].

$$\tau_{(ijk)[lmn]} = \frac{\left[l\left(\begin{array}{c}i\sigma_{xx}+\\j\sigma_{xy}+k\sigma_{xz}\end{array}\right)+m\left(\begin{array}{c}i\sigma_{yx}+\\j\sigma_{yy}+k\sigma_{yz}\end{array}\right)+n\left(\begin{array}{c}i\sigma_{zx}+\\j\sigma_{zy}+k\sigma_{zz}\end{array}\right)\right]}{\sqrt{(i^2+j^2+k^2)(l^2+m^2+n^2)}} \quad (9)$$

In this disclosure, of the 12 types of shear stresses obtained as described above, the highest shear stress was adopted as the thermal stress τ applied to the silicon wafer in heat treatment of the device fabrication process.

The thermal stress τ applied to the silicon wafer in heat treatment of the device fabrication process can be determined by simulation calculation instead of being determined using a heat treatment unit as described above. Thus, the thermal stress τ can be estimated simply in a short time. Specifically, the radiant heat applied to the wafer from a heater and the heat conduction are analyzed by the finite element method, and the temperature distribution in the wafer plane in the heat treatment process is obtained. From the obtained temperature distribution, the thermal stress τ can be determined using the formulae (7), (8), and (9).

After that, in Step S4, whether or not slip dislocations are formed in the silicon wafer W in the device fabrication process is determined. In this disclosure, when the thus obtained thermal stress τ applied to the silicon wafer W in the device fabrication process is equal to or higher than the critical shear stress $\tau_{cri}$ determined by the formula (6), slip dislocations are formed in the silicon wafer in the device fabrication process, and silicon wafers determined to have slip dislocations formed therein are determined to be defective products. In other words, when the thermal stress τ is lower than the critical shear stress $\tau_{cri}$, slip dislocations are determined not to be formed even after heat treatment of the device fabrication process is performed, and silicon wafers determined to have no slip dislocations formed therein are determined to be good products.

In such a way, whether or not slip dislocations are formed after performing heat treatment of the device fabrication process is determined with high accuracy, so that the quality (pass/fail) of a silicon wafer can be determined.

In the above embodiment of the quality evaluation method for a silicon wafer, the critical shear stress $\tau_{cri}$ is expressed by the sum of the effect $\tau_{\Delta Oi}$ of the precipitated oxygen concentration $\Delta O_i$ on the critical shear stress $\tau_{cri}$ expressed by the above formula (3) and the effect $\tau_{SL}$ of change in the residual oxygen concentration $C_O$ on the critical shear stress $\tau_{cri}$ expressed by the formula (4) (formula (5)).

The inventors diligently studied to determine the critical shear stress $\tau_{cri}$ with higher accuracy and subsequently found room for improvement in the calculation of the effect $\tau_{SL}$ of change in the residual oxygen concentration $C_O$ on the critical shear stress $\tau_{cri}$. Further, they found that the effect of change in the residual oxygen concentration $C_O$ on the critical shear stress $\tau_{cri}$ can be calculated with higher accuracy using $\tau_{SL}'$ expressed by the formula (10) below instead of using the above formula (4).

$$\tau_{SL}' = B \times \epsilon^{0.22} \times C_O \times \exp(0.91 \text{ eV}/kT) \quad (10),$$

where B is a constant, ε is the distortion velocity, k is the Boltzmann constant, and T is the temperature.

Expressing the critical shear stress $\tau_{cri}$ as the sum of the effect $\tau_{\Delta Oi}$ of the precipitated oxygen concentration $\Delta O_i$ on the critical shear stress $\tau_{cri}$ expressed by the above formula (3) and the effect $\xi_{SL}$ of change in the residual oxygen concentration $C_O$ on the critical shear stress $\tau_{cri}$ expressed by the above formula (10) allows the critical shear stress $\tau_{cri}$ to be determined with higher accuracy.

$$\tau_{cri} = \tau_{\Delta Oi} + \tau_{SL}' = A(1/\Delta O_i) + B \times \epsilon^{0.22} \times C_O \times \exp(0.91 \text{ eV}/kT) \quad (11)$$

(Method of Producing Silicon Wafer)

A method of producing a silicon wafer will now be described. In the disclosed method of producing a silicon wafer, a single crystal silicon ingot is grown under the growing conditions allowing a silicon wafer to be obtained, which wafer is determined to have no slip dislocations formed in a device fabrication process by the above quality evaluation method for a silicon wafer, and the grown single crystal silicon ingot is subjected to a wafer processing process.

Figure 9:
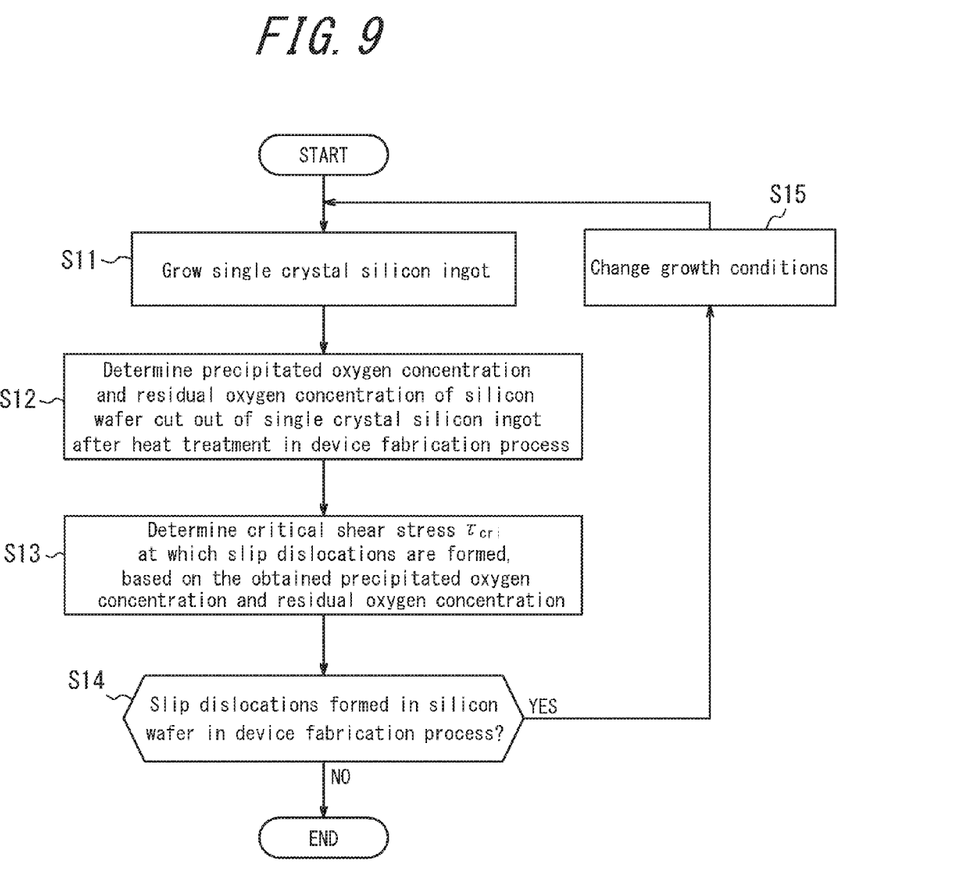
FIG. 9 is a flowchart of one embodiment of a method of producing a silicon wafer.

FIG. 9 shows a flowchart of one embodiment of a method of producing a silicon wafer. The steps of the method will be described below in accordance with this flowchart. First, a single crystal silicon ingot I is grown in Step S11. The growth of the single crystal silicon ingot I can be performed by the CZ process or the floating zone melting (FZ) process. In the growth of the single crystal silicon ingot I, the oxygen concentration, the carbon concentration, the nitrogen concentration, and the like can be suitably adjusted so that the silicon wafer W cut out of the grown silicon ingot I will have the desired characteristics. Further, suitable dopants may be added to obtain a wafer having a conductivity type of n-type or p-type.

The grown single crystal silicon ingot I is subjected to a known processing process including peripheral grinding, slicing, lapping, etching, and mirror polishing, thereby obtaining a silicon wafer W having a predetermined thickness.

The subsequent steps from Step S12 to Step S14 correspond to Steps S2 to S4 in FIG. 1, respectively. Those steps relate to the above-described quality evaluation method for a silicon wafer, so the description will not be repeated.

In this disclosure, in Step S14, when whether or not slip dislocations are formed in the silicon wafer W in the device fabrication process can be determined with high accuracy, and the thermal stress τ applied to the silicon wafer W in the device fabrication process is equal to or higher than the critical shear stress $\tau_{cri}$ determined by the formula (6), slip dislocations are determined to be formed in the silicon wafer in the device fabrication process. In other words, when the thermal stress τ is lower than the critical shear stress $\tau_{cri}$, slip dislocations are determined not to be formed even after heat treatment of the device fabrication process is performed.

Further, a single crystal silicon ingot is grown under the growing conditions allowing a silicon wafer to be obtained, which wafer is determined to have no slip dislocations formed in a device fabrication process in Step S14, and the grown single crystal silicon ingot is subjected to a wafer processing process, thereby obtaining a silicon wafer in which slip dislocations are not formed in the device fabrication process.

When the thermal stress τ is equal to or higher than the critical shear stress $\tau_{cri}$ in Step S14, the growth conditions for the single crystal silicon ingot are changed, and the steps from Step S11 in which a single crystal silicon ingot is grown to Step S14 in which whether or not slip dislocations are formed in the device fabrication process is determined are repeated until the thermal stress τ becomes lower than the critical shear stress $\tau_{cri}$ in Step S15.

The growth conditions for the single crystal silicon ingot I are changed specifically so that the critical shear stress $\tau_{cri}$ will increase, the precipitated oxygen concentration $\Delta O_i$ will decrease, and/or the residual oxygen concentration $C_O$ will decrease. When the single crystal silicon ingot I is grown, for example, by the CZ process, the above change can be performed, for example, by changing the oxygen concentration, the nitrogen concentration, or the carbon concentration or by changing the rotational speed of a crucible, the pulling rate, or the like.

Note that when the precipitated oxygen concentration $\Delta O_i$ and the residual oxygen concentration $C_O$ after heat treatment performed in the device fabrication process are determined by simulation calculation, the process of Steps S12 to S14 is performed without growing the single crystal silicon ingot I in Step S11; a single crystal silicon ingot is grown under the growth conditions under which a silicon wafer determined to have no slip dislocations formed can be obtained in the end; and the grown single crystal silicon ingot is subjected to a wafer processing process. Thus, a silicon wafer in which slip dislocations are not formed in the device fabrication process can be obtained.

The precipitated oxygen concentration $\Delta O_i$ after the heat treatment in the device fabrication process is preferably controlled to $0.06 \times 10^{17}$ atoms/cm³ or more and $0.8 \times 10^{17}$ atoms/cm³ or less. This can prevent slip dislocations from being formed even if a high stress is applied at a high temperature. Further, the residual oxygen concentration $C_O$ after the heat treatment in the device fabrication process is preferably controlled to $10 \times 10^{17}$ atoms/cm³ or more and $18 \times 10^{17}$ atoms/cm³ or less. This can prevent slip dislocations from being formed even if a high stress is applied at a high temperature.

Thus, a silicon wafer in which slip dislocations are not formed after heat treatment in the device fabrication process can be produced.

(Silicon Wafer)

Next, a silicon wafer of this disclosure will be described. The disclosed silicon wafer is a silicon wafer having a precipitated oxygen concentration $\Delta O_i$ and a residual oxygen concentration $C_O$ at which the thermal stress τ applied in a device fabrication process is lower than the critical shear stress $\tau_{cri}$ at which slip dislocations are formed in the device fabrication process, in which wafer, no slip dislocations are formed even after a heat treatment of the device fabrication process is performed.

For a silicon wafer according to this disclosure, the precipitated oxygen concentration $\Delta O_i$ after heat treatment in the device fabrication process is preferably $0.06 \times 10^{17}$ atoms/cm³ or more and $0.8 \times 10^{17}$ atoms/cm³ or less. This can prevent slip dislocations from being formed even if a high stress is applied at a high temperature. Further, the residual oxygen concentration $C_O$ after heat treatment of the device fabrication process is preferably $10 \times 10^{17}$ atoms/cm³ or more and $18 \times 10^{17}$ atoms/cm³ or less. This can prevent slip dislocations from being formed even if a high stress is applied at a high temperature.

Example 1

Examples of this disclosure will now be described.

At a set temperature, a high-temperature four-point bending test capable of applying a given stress was performed.

Figure 10:
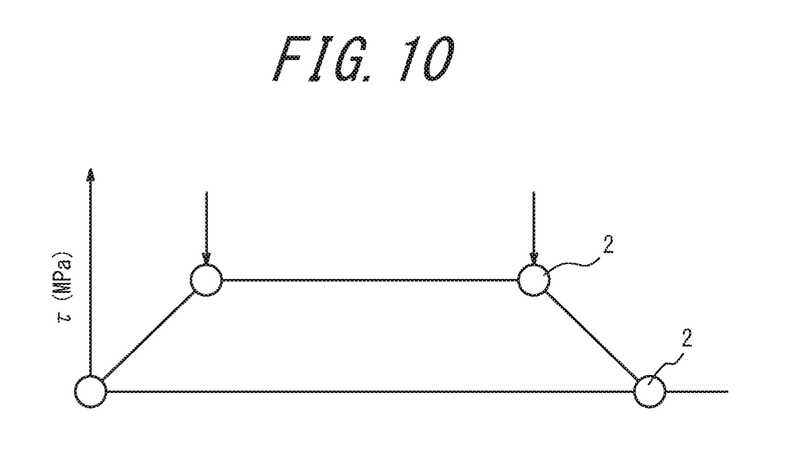
FIG. 10 is a diagram showing the profile of the stress applied to sample wafers in a high-temperature four-point bending test.

The high-temperature four-point bending test is a test method in which the point of action in the above-described high-temperature three-point bending test is doubled, and a stress is applied with the distance between the two points of action being 15 mm. A characteristic of the high-temperature four-point bending test is that a constant stress can be applied to a sample piece as shown in the stress profile diagram of FIG. 10. Accordingly, this is an effective technique for examining whether or not slip dislocations are formed. The high-temperature four-point bending test was performed using a number of samples having different BMD densities, initial oxygen concentrations, residual oxygen concentrations $C_O$, and precipitated oxygen concentrations $\Delta O_i$ as shown in Table 1 under the conditions shown in Table 2. Here, the oxygen concentration of each sample wafer was measured based on the infrared absorption spectroscopy in accordance with ASTM F121-1979 using Fourier transform infrared spectrometry.

TABLE 1

| BMD density (/cm³) | Initial oxygen concentration InO$_i$ (×10$^{17}$ atoms/cm³) | Residual oxygen concentration C$_O$ (×10$^{17}$ atoms/cm³) | Precipitated oxygen concentration ΔO$_i$ (×10$^{17}$ atoms/cm³) |
|---|---|---|---|
| 5.00E+09 | 10 | 9.9 | 0.1 |
| 5.00E+09 | 10 | 9.2 | 0.8 |
| 5.00E+09 | 10 | 8.8 | 1.2 |
| 5.00E+09 | 10 | 8.5 | 1.5 |
| 5.00E+09 | 10 | 8.0 | 2.0 |
| 5.00E+09 | 10 | 5.8 | 4.2 |
| 5.00E+09 | 10 | 5.0 | 5.0 |
| 5.00E+09 | 10 | 3.3 | 6.7 |
| 1.00E+10 | 12 | 11.9 | 0.1 |
| 1.00E+10 | 12 | 11.2 | 0.8 |
| 1.00E+10 | 12 | 10.0 | 2.0 |
| 1.00E+10 | 12 | 9.5 | 2.5 |
| 1.00E+10 | 12 | 8.3 | 3.7 |
| 1.00E+10 | 12 | 7.8 | 4.2 |
| 1.00E+10 | 12 | 6.7 | 5.3 |
| 1.00E+10 | 12 | 5.0 | 7.0 |
| 1.00E+10 | 12 | 3.1 | 8.9 |
| 1.50E+10 | 15 | 14.9 | 0.1 |
| 1.50E+10 | 15 | 13.8 | 1.2 |
| 1.50E+10 | 15 | 13.0 | 2.0 |
| 1.50E+10 | 15 | 11.5 | 3.5 |
| 1.50E+10 | 15 | 10.2 | 4.8 |
| 1.50E+10 | 15 | 9.2 | 5.8 |
| 1.50E+10 | 15 | 8.1 | 6.9 |
| 1.50E+10 | 15 | 5.9 | 9.1 |
| 1.50E+10 | 15 | 3.8 | 11.2 |
| 1.50E+10 | 18 | 17.9 | 0.1 |
| 1.50E+10 | 18 | 16.0 | 2.0 |
| 1.50E+10 | 18 | 13.8 | 4.2 |
| 1.50E+10 | 18 | 12.1 | 5.9 |
| 1.50E+10 | 18 | 11.2 | 6.8 |
| 1.50E+10 | 18 | 9.0 | 9.0 |
| 1.50E+10 | 18 | 6.0 | 12.0 |

TABLE 2

| Test temperature (° C.) | Load stress (MPa) |
|---|---|
| 700 | 80 |
| 700 | 60 |
| 700 | 40 |
| 900 | 20 |
| 900 | 10 |
| 900 | 5 |
| 1100 | 5 |
| 1100 | 3 |
| 1100 | 1.5 |

Figure 11:
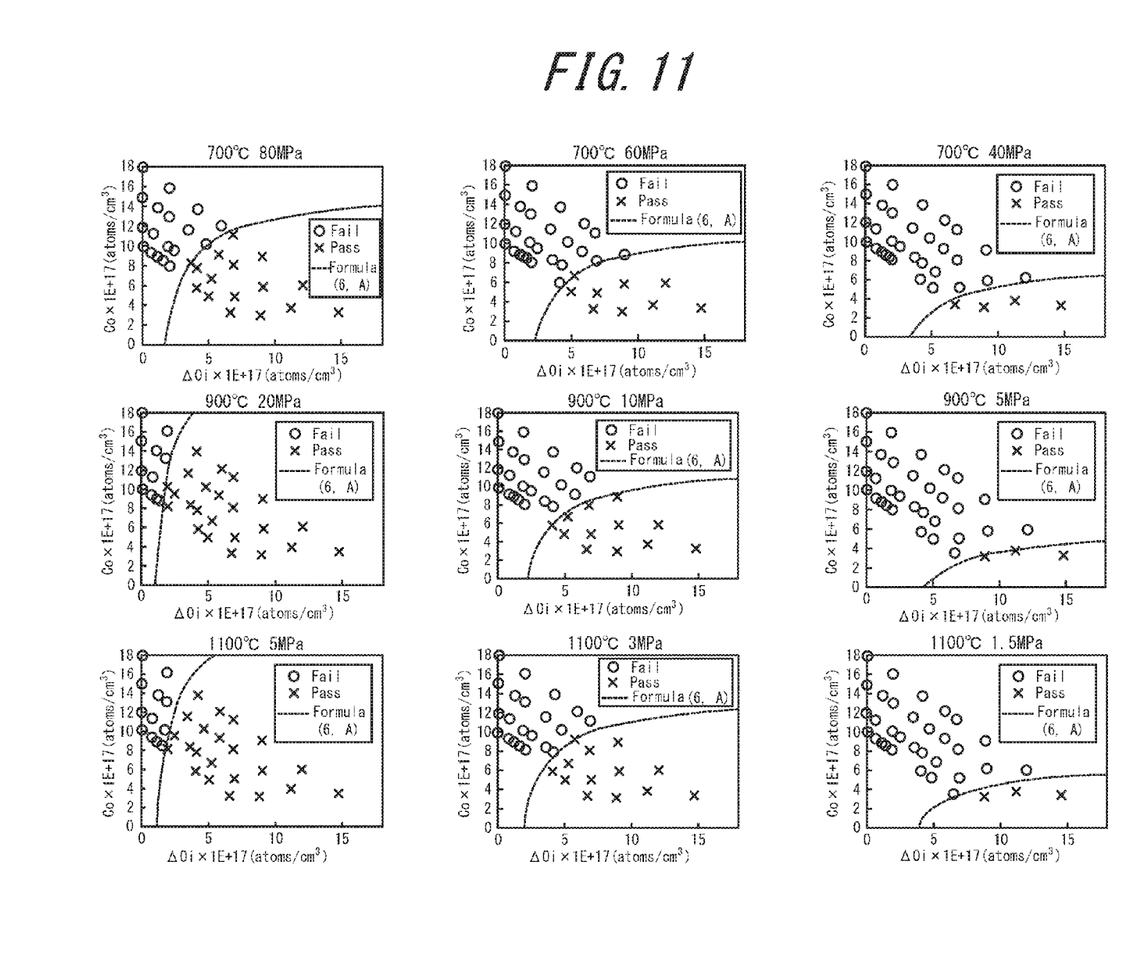
FIG. 11 is a diagram showing that the present invention can determine with high accuracy whether or not slip dislocations are formed in the device fabrication process.

Then, it was determined whether or not slip dislocations had been formed from BMDs after each sample wafer was loaded with a stress by subjecting each sample wafer to selective etching and then confirming the presence or absence of dislocation pits using an optical microscope. Whether or not slip dislocations were formed is shown in FIG. 11, in which the precipitated oxygen concentration $\Delta O_i$ is represented by the horizontal axis and the residual oxygen concentration $C_O$ is represented by the vertical axis. In each graph in the diagram, each "o" indicates a sample wafer in which no slip dislocations were confirmed to be formed, and each "x" indicates a sample wafer in which slip dislocations were confirmed to be formed. Further, the broken line in each graph is a line obtained by calculating $C_O$ by assigning the applied stress to $\tau_{cri}$ and the precipitated oxygen concentration to $\Delta O_i$ in the formula (6).

As can be seen from the formula (6), in each sample wafer under the above broken line, the critical shear stress $\tau_{cri}$ is lower than the thermal stress $\tau$ applied to the silicon wafer in the device fabrication process. In this disclosure, such a wafer is determined as a silicon wafer in which slip dislocations are formed. As is apparent from FIG. 11, the broken line in each graph forms a boundary between the sample wafers in which slip dislocations were formed and the sample wafers in which slip dislocations were not formed. This shows that the formula (6) makes it possible to determine with high accuracy the critical shear stress at which slip dislocations were formed after heat treatment performed in the device fabrication process, thereby determining the presence or absence of the slip dislocations with high accuracy.

Example 2

Sample wafers were subjected to heat treatment designed to emulate a standard device fabrication process, and whether or not slip dislocations were formed from BMDs was determined. Here, the heat treatment in the emulated device fabrication process was constituted by two processes A and B. Here, the process A was constituted by four heat treatment steps, in which different baking temperatures and heat treatment times were used. Meanwhile, the process B was constituted by six heat treatment steps, in which different baking temperatures and heat treatment times were used as in the process A, and the last step was an RTA step.

In the process A, the loading temperature and the unloading temperature of a sample wafer were both 600° C. and the heating rate and the cooling rate were both 8° C./min in the first to third steps. The loading temperature and the unloading temperature of the sample wafer were 800° C., and the heating rate and the cooling rate were 15° C./min in the fourth step. In the process B, the loading temperature and the unloading temperature of the sample wafer were both 600° C., and the heating rate and the cooling rate were both 8° C./min in the first to fifth steps; and the loading temperature and the unloading temperature of the sample wafer were both 650° C., the heating rate was 150° C./s, and the cooling rate was 75° C./s in the sixth step. The heat treatment conditions in the processes A and B are shown in Tables 3 and 4, respectively. The initial oxygen concentration $InO_i$, the residual oxygen concentration $C_O$, and the precipitated oxygen concentration $\Delta O_i$ of the sample wafers having been subjected to the processes A and B are shown in Tables 5 and 6, respectively.

TABLE 3

| Step | Heat treatment temperature (° C.) | Heat treatment time (min) |
|---|---|---|
| 1 | 650 | 100 |
| 2 | 900 | 20 |
| 3 | 1150 | 600 |
| 4 | 1100 | 240 |

TABLE 4

| Step | Heat treatment temperature (° C.) | Heat treatment time (min) |
|---|---|---|
| 1 | 650 | 100 |
| 2 | 900 | 20 |
| 3 | 825 | 30 |
| 4 | 750 | 100 |
| 5 | 1050 | 60 |
| 6 (RTA) | 1000 | 1 |

TABLE 5

| Initial oxygen concentration $InO_i$ ($\times 10^{17}$ atoms/cm$^3$) | Residual oxygen concentration $C_O$ ($\times 10^{17}$ atoms/cm$^3$) | Percipitated oxygen concentration $\Delta O_i$ ($\times 10^{17}$ atoms/cm$^3$) | Critical shear stress $\tau_{cri}$ obtained by Formula (6) (MPa) | $\tau_{cri} > \tau$ | Slip dislocations | |
|---|---|---|---|---|---|---|
| 13.0 | 6.9 | 6.1 | 5.1 | Not satisfied | Formed | Sample wafer 1 |
| 12.2 | 7.6 | 4.6 | 6.5 | Satisfied | Not formed | Sample wafer 2 |
| 11.8 | 8.6 | 3.2 | 9.0 | Satisfied | Not formed | Sample wafer 3 |

TABLE 6

| Initial oxygen concentration $InO_i$ ($\times 10^{17}$ atoms/cm$^3$) | Residual oxygen concentration $C_O$ ($\times 10^{17}$ atoms/cm$^3$) | Percipitated oxygen concentration $\Delta O_i$ ($\times 10^{17}$ atoms/cm$^3$) | Critical shear stress $\tau_{cri}$ obtained by Formula (6) (MPa) | $\tau_{cri} > \tau$ | Slip dislocations | |
|---|---|---|---|---|---|---|
| 13.4 | 10.6 | 2.8 | 11.8 | Not satisfied | Formed | Sample wafer 4 |
| 12.3 | 10.8 | 1.5 | 19.4 | Satisfied | Not formed | Sample wafer 5 |
| 10.7 | 9.8 | 0.9 | 30.0 | Satisfied | Not formed | Sample wafer 6 |

For the thermal stress $\tau$ in the device fabrication process, the in-place temperature of each sample wafer loaded into a heat treatment furnace was measured with a thermocouple using the formulae (7) to (9). A stress of 5.5 MPa was applied at a baking temperature of 1100° C. in the fourth step in the process A. Meanwhile, a thermal stress of 16.1 MPa was found to be applied at a baking temperature of 1000° C. in the sixth step in the process B.

With respect to the sample wafers having been subjected to the processes A and B, Table 5 shows the results of determining whether or not the thermal stress τ applied to each silicon wafer in heat treatment of the device fabrication process was lower than $\tau_{cri}$ calculated using the formula (6) and Table 6 shows the results of whether or not slip dislocations were actually formed.

As described above, in this disclosure, when the thermal stress applied to a sample wafer in heat treatment of a device fabrication process is lower than the critical shear stress $\tau_{cri}$, i.e., when $\tau < \tau_{cri}$ is satisfied; slip dislocations are determined not to be formed in the silicon wafer on which heat treatment is performed in the device fabrication process. As is apparent from Tables 5 and 6, the evaluation results according to this disclosure are completely consistent with the results of whether or not slip dislocations were actually formed. This shows that whether or not slip dislocations originated from BMDs are formed can be determined using the formula (6) with high accuracy.

Further, a single crystal silicon ingot was grown at a lower oxygen concentration than the case of growing sample wafers 1 and 3 in which slip dislocations were formed in Tables 5 and 6. The critical shear stress $\tau_{cri}$ of a silicon wafer W having a lower initial oxygen concentration taken out of the grown ingot was determined based on the precipitated oxygen concentration $\Delta O_i$ and the residual oxygen concentration after heat treatment in the device fabrication process. Consequently, the critical shear stress $\tau_{cri}$ was higher than that obtained under the unchanged growth conditions, i.e., where $\tau < \tau_{cri}$ was satisfied. Thus, the silicon wafer W was obtained, in which no slip dislocations were formed even after heat treatment in the device fabrication process was performed thereon.

INDUSTRIAL APPLICABILITY

The critical shear stress at which slip dislocations are formed in a device fabrication process is determined with high accuracy, thereby determining with high accuracy whether or not slip dislocations are formed in a silicon wafer due to heat treatment of the device fabrication process. Accordingly, this technique is useful in the semiconductor industry.

The invention claimed is:

1. A quality evaluation method for a silicon wafer, comprising:
   determining a precipitated oxygen concentration and a residual oxygen concentration in the silicon wafer after heat treatment performed in a device fabrication process;
   determining a critical shear stress $\tau_{cri}$ at which slip dislocations are formed in the silicon wafer in the device fabrication process based on the determined precipitated oxygen concentration and residual oxygen concentration; and
   comparing the determined critical shear stress $\tau_{cri}$ to a thermal stress τ applied to the silicon wafer in the heat treatment of the device fabrication process, whereby determining that slip dislocations are formed in the silicon wafer in the device fabrication process when the thermal stress τ is equal to or more than the critical shear stress $\tau_{cri}$, or determining that slip dislocations are not formed in the silicon wafer in the device fabrication process when the thermal stress τ is less than the critical shear stress $\tau_{cri}$,
   wherein:

$\tau_{cri} = 24.6 \times (1/\Delta O_i) + 7.0 \times 10^{-5} \times C_O \times \exp(0.91\ eV/kT)$ where:
   $\Delta O_i$=the precipitated oxygen concentration,
   $C_O$=the residual oxygen concentration,
   T=the temperature of the heat treatment, and
   k=the Boltzmann constant.

2. The quality evaluation method for a silicon wafer according to claim 1, wherein determining the precipitated oxygen concentration $\Delta O_i$ and the residual oxygen concentration $C_O$ after heat treatment in the device fabrication process is performed by measuring the precipitated oxygen concentration and the residual oxygen concentration in the silicon wafer after the heat treatment performed on the silicon wafer in the device fabrication process.

3. The quality evaluation method for a silicon wafer according to claim 1, wherein determining the precipitated oxygen concentration and the residual oxygen concentration $C_O$ after the heat treatment in the device fabrication process is performed by simulation calculations.

4. The quality evaluation method for a silicon wafer according to claim 1, wherein the thermal stress τ is estimated based on a temperature distribution in a radial direction of the silicon wafer having been heated in a heat treatment unit.

5. The quality evaluation method for a silicon wafer according to claim 1, wherein the thermal stress τ is estimated by simulation calculations.

6. A method of producing a silicon wafer, comprising:
   growing a single crystal silicon ingot under growing conditions that allow a silicon wafer to be obtained, which wafer is determined to have no slip dislocations formed in a device fabrication process by the quality evaluation method for a silicon wafer, according to claim 1; and
   subjecting the grown single crystal silicon ingot to a wafer processing process.

7. The method of producing a silicon wafer according to claim 6, wherein the precipitated oxygen concentration after heat treatment in the device fabrication process is $0.06 \times 10^{17}$ atoms/cm$^3$ or more and $0.8 \times 10^{17}$ atoms/cm$^3$ or less.

8. The method of producing a silicon wafer according to claim 6, wherein the residual oxygen concentration after heat treatment in the device fabrication process is $10 \times 10^{17}$ atoms/cm$^3$ or more and $18 \times 10^{17}$ atoms/cm$^3$ or less.

* * * * *